United States Patent [19]

Williams

[11] Patent Number: 4,688,638
[45] Date of Patent: Aug. 25, 1987

[54] DOWNHOLE CORROSION COUPON HOLDER

[75] Inventor: Mitchel E. Williams, Lafayette, La.

[73] Assignee: Conoco Inc., Ponca City, Okla.

[21] Appl. No.: 866,859

[22] Filed: May 23, 1986

[51] Int. Cl.$^4$ .................................... E21B 47/00
[52] U.S. Cl. ........................... 166/250; 73/86; 166/242; 166/902; 436/6
[58] Field of Search .......... 166/250, 902, 113, 242, 166/208; 436/6; 422/53; 73/86, 432 B, 432.1

[56] References Cited

U.S. PATENT DOCUMENTS

| | | | |
|---|---|---|---|
| 1,683,489 | 9/1928 | Rice | 73/86 |
| 2,994,778 | 8/1961 | Marsh | 73/86 X |
| 3,384,181 | 5/1968 | Maly et al. | 166/250 X |
| 3,451,264 | 6/1969 | Kastor | 166/250 X |
| 4,267,148 | 5/1981 | Dickson et al. | 436/6 X |
| 4,483,397 | 11/1984 | Gray | 166/250 |
| 4,505,331 | 3/1985 | Akkerman | 166/117.5 |
| 4,524,833 | 6/1985 | Hilts et al. | 166/117.5 X |
| 4,603,113 | 7/1986 | Bauer | 166/902 X |

*Primary Examiner*—George A. Suchfield
*Attorney, Agent, or Firm*—Richard K. Thomson

[57] ABSTRACT

A corrosion coupon anchoring system for positively positioning a corrosion monitoring coupon in the production flowpath downhole in a producing well. Preferably cylindrical coupons are held firmly within a cylindrical housing suspended out of contact with any other metallic surface. An adaptor threadingly engages the cylindrical housing to a conventional locking mandrel that is locked in place to a nipple positioned in the tubing string. The minimum internal dimension of the coupon holding section is not less than the minimum internal dimension of the locking mandrel so as to minimize flow restriction introduced by the anchoring system.

19 Claims, 4 Drawing Figures

DOWNHOLE CORROSION COUPON HOLDER

BACKGROUND AND SUMMARY OF THE PRESENT INVENTION

The present invention relates to a method and apparatus for anchoring corrosion coupons downhole in the production tubing of a producing oil and/or gas well. More particularly, the present invention is directed to a method and apparatus which makes it possible to closely duplicate the actual conditions experienced by the production tubing to enable a more accurate evaluation of corrosion rate and, hence, operative life of the tubing, to be made.

Monitoring the corrosive effects of well fluids using corrosion coupons allows (1) a determination of the corrosion problem downhole to be made in the actual environment (pressure, temperature, etc.) to which the production tubing is exposed, (2) an evaluation of the effectiveness of the corrosion mitigation program to be conducted, and (3) an assessment of the life of the production tubing to be made.

Failure to monitor corrosion rates and to take appropriate measure to slow those rates can reduce the operative life of the well. Accordingly, monitoring the corrosive effects of the corrosives entrained in the well fluids (such as $CO_2$, $H_2S$ and $O_2$) is becoming increasingly important. A number of coupon holders for positioning corrosion coupons downhole are currently available on the market today. The prior art systems of which applicant is aware suffer from one or more of the following defects: (1) the coupon holder can only be used where the well is capable of accomodating specially configured tubing (i.e., a side-pocket mandrel); (2) the conditions (pressure, flow rate, etc.) experienced by the coupon are not representative of those experienced by the tubing—thus, the corrosion rate may also differ; (3) the anchoring technique within the tubing may be unreliable and/or potentially harmful to the interior surface of the tubing; (4) the manner of securing the coupon in the holder is such that it effectively alters the corrosion rate impairing the accuracy of the monitoring system; and (5) the holder may unduly restrict the flow of fluids therethrough, which both reduces the rate of recovery of fluids and alters the flow and corrosion conditions experienced by the coupon (i.e., gives a faulty indication of corrosion rate).

The present invention overcomes these deficiencies of the prior art. A preferably cylindrical coupon is anchored in one or more predetermined locations within the production tubing using state-of-the-art nipples and locking mandrels. The holder which houses the coupon is threadingly attached to an adaptor which, in turn, is threaded onto the end of the locking mandrel. The coupon is maintained in position within the cylindrical housing by end retainers which telescopically receive the ends of the coupon and which are compressively engaged by the end of the housing and the end of the adaptor. This compressive force is sufficient to firmly engage the coupon but is not excessive to the point of deforming the coupon or the end retainers. The amount of compressive force exerted is limited by metal to metal engagement between the adapter and the coupon holder. Further, the metallic coupons are maintained in positioned out of contact with any other metallic surface or object.

Preferably, two or more coupons are used. In this manner, it is possible to cross-check the corrosion experienced by each. The two coupons can be made of the same material for purposes of cross-checking or they may be made of different materials in order to determine how different alloys are affected by the same environment. With two coupons, a center retainer is telescoped over the adjoining ends of the coupons to maintain proper alignment. The minimum dimension inside the housing occupied by the coupon is not less than the minimum internal dimension of the locking mandrel so as to minimize the impediment of flow caused by the holder.

Accordingly, the coupon holder of the present invention provides a corrosion monitoring system that (1) is firmly anchored in position, (2) does not damage the internal surface of the casing, (3) does not require specially configured tubing but, rather, utilizes a conventional nipple that is ordinarily positioned within the tubing string to permit other types of periodic downhole operations, (4) minimizes the obstruction of fluid flow, (5) substantially duplicates the flow conditions experienced by the actual tubing so as to provide an accurate reading of corrosion rate and, (6) is secured by means not requiring a penetrating metallic fastener or contact by any other metallic object which can unduly alter corrosion due to cathodic reaction or the resulting internal strain within the coupon and, (7) has a securing means that permit back-flow around the coupon to increase the surface area exposed to the corrosive fluids.

Various other features, characteristics and advantages of the present invention will become apparent after a reading of the following detailed description.

DETAILED DESCRIPTION OF THE PREFERRED EMBODIMENTS

Figure 2:
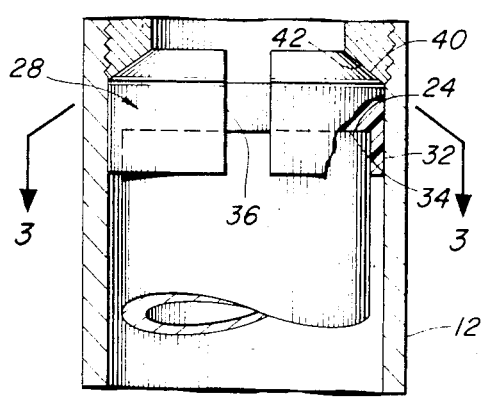
FIG. 2 is an enlarged sectional side view depicting the end and center retainers of the coupon holder of the present invention in greater detail.
Figure 2:
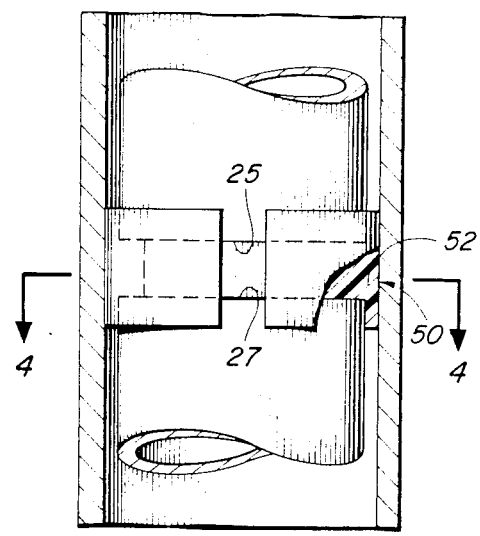
Figure 4:
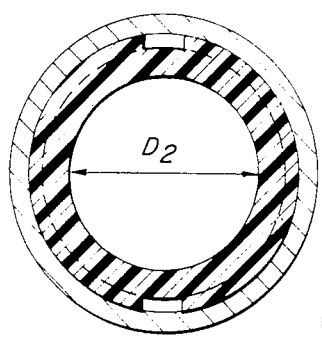
FIG. 4 is a lateral cross-section as seen along line 4—4 of FIG. 2.
Figure 3:
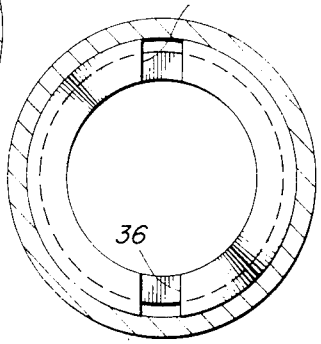
FIG. 3 is a lateral cross-section as seen long line 3—3 of FIG. 2.
Figure 1:
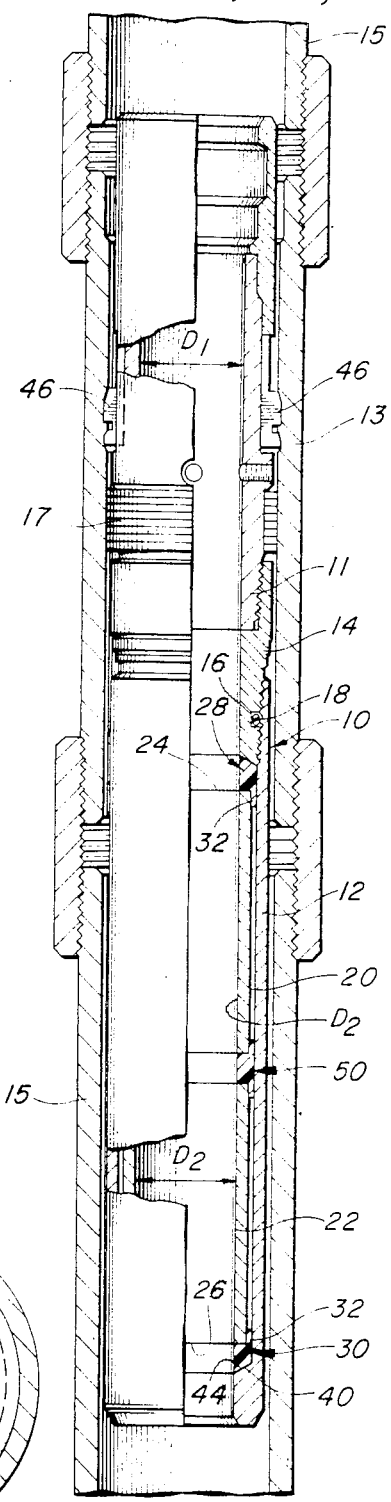
FIG. 1 is a cross-sectional side view with portions broken away, of the coupon holder of the present invention suspended in a nipple by a locking mandrel.

The corrosion coupon anchoring system of the present invention is depicted in FIG. 1 generally at 10. While this corrosion coupon anchor system cannot be used with rod pumped wells, it could be utilized in virtually every other type of producing oil or gas well. Cylindrical housing 12 threadingly engages adaptor 14 which is, in turn, threaded on to the end of a locking mandrel 11. The use of the adaptor 14 enables the corrosion coupon holder of the present invention to be utilized with any commercially available locking mandrel without the need to modify the tool. One such mandrel, by way of example and not limitation, is identified as type 'X' lock and is sold by Otis Engineering Corporation. This locking mandrel 11 is lowered into a tubing string by a wireline and is set into a type 'X' nipple 13 which has been inserted in the tubing string at a predetermined location to permit various downhole operations such as this to be subsequently performed, as necessary. Mandrel 11 has a minimum internal dimension $D_1$. Resilient packing 17 forms a fluidic seal between mandrel 11 and nipple 13 preventing fluid flow outside of mandrel 11.

A groove 16 interrupts the threads on adaptor 14. Groove 16 receives an O-ring 18 which exerts pressure against the internal surface of cylindrical housing 12 discouraging thread disengagement. There are preferably at least two coupons 20 and 22 secured within the housing 12 (shown here in their preferred cylindrical configuration). While these coupons could be manufactured of different materials to determine which is more corrosion resistant in a particular environment, it is preferred that the two coupons both be made of the same material and that that material be the same material as the tubing. Examples of suitable materials are 1020 and 4140 alloy steels. The use of two coupons of the same material enables a cross check to be made on the nature and rate of corrosion.

The distal ends 24 and 26 of coupons 20 and 22 are each engaged by identical end retainers 28 and 30. Each end retainer comprises a cylindrical sleeve 32 which slides over the end 24 or 26 of coupon 20 or 22. Shoulder 34 limits the distance which sleeve 32 can slide over its respective coupon end. Lateral slots 36 and 38 provide flow paths for the corrosive liquids on the exterior of the coupon. This back flow has the benefits of (a) increasing the surface area of the coupons exposed to the fluids and (b) will provide a means to distinguish between the combined corrosion/erosion effects inside the coupon and the almost purely erosive effects outside the coupon. The opposite end of end retainers 28 and 30 are beveled as at 40 for engagement by correspondingly beveled surfaces 42 and 44 provided on the end of adaptor 14 and cylindrical housing 12, respectively.

When two coupons are utilized, a center retainer 50 telescopically receives the proximate ends 25 and 27 of coupons 20 and 22. Center rib 52 fits between ends 25 and 27 to keep the coupons separated. Retainers 28, 30 and 50 are preferably made of a plastic material such as Ryton (a registered trademark of Phillips Petroleum Co.) polymer. Non-metalic fasteners are used in order to avoid cathodic reaction which may occur as a result of two dissimilar metals coming in contact. In fact, end retainers 28 and 30 and center retainer 50 securely suspend coupons 20 and 22 out of contact with even the cylindrical housing 12 which may be made of, by way of example, Inconel 318 (a registered trademark of International Nickel Company) alloy steel. The minimum internal dimension $D_2$ of the portion of housing 12 that contains the coupons 20 and 22 (usually inner diameter of the coupons themselves) is not less than $D_1$.

To utilize the coupon holder of the present invention, a properly sized locking mandrel 11, adaptor 14 and cylindrical housing 12 are selected for the type and size of nipple 13 and tubing 15. The corresponding sizes of coupons 20, 22 (preferably cylindrical) and end and center retainers 28, 30 and 50 are thereby determined. The corrosion coupon anchoring system 10 is configured by assembling end retainers 28 and 30, center retainer 50 and corrosion coupons 20 and 22 within cylindrical housing 12. Adaptor 14 is then threaded into housing 12. When the threads are fully seated (i.e., when the end of adaptor 14 dogs down against the internal shoulder in holder 10), the beveled surface 42 on adaptor 14 in conjunction with beveled surface 44 on housing 12, maintain a firm compressive force on the coupon assembly but do not cause deformation or significant internal strain in any component. The coupon anchoring system 10 of the present invention forms no greater restriction of flow than the locking mandrel 11 since its minimum internal dimension $D_2$ is not less than the minimum internal dimension $D_1$ of said mandrel 11.

Adaptor 14 is then threaded onto the appropriate locking mandrel and the entire system 10 is lowered downhole using a wireline apparatus. When the corrosion coupon anchoring system is in the vicinity of the nipple, locking fingers 46 are sprung into engagement position as shown in FIG. 1, by using a conventional jarring technique to shear a retainer pin (not shown). The anchoring system is, then, left downhole during normal production operations for a period of several months. System 10 can then be fished out of the wellbore using conventional wireline techniques. The coupons are then weighed individually (after cleaning) and their net weights compared to their original gross weights at the time of insertion into the well. The coupons can also be subdivided and microscopically examined to deterine the type and source of corrosion, as well as the rate.

A prototype coupon holder of the present invention was tested in a gas well that is approximately 150 miles off the Louisiana coast. Two coupons, both of 1020 alloy steel and identified as C-1018-1 and C-1018-2, where inserted at the 6142 foot mark of a well that is in excess of 9000 feet deep using an Otis 'X' locking mandrel in a type 'X' nipple. These coupons are downhole for a period of 67 days, 21 days of which the well was producing (the well was periodically shut in for the remainder of the time for rate control). The well, which was flowing at a rate of 11 million cubic feet of gas and 260 barrels of condensate per day, experienced no appreciable flow reduction due to the insertion of the coupon holder.

The coupons were removed from the holder and after a thorough cleansing, each coupon was weighed to determine the amount of weight lost due to corrosion/erosion effects. The weight loss was plugged into the following formula to determine corrosion rate:

$$c = k \cdot \frac{\Delta m}{A \cdot t \cdot \rho}$$

where
c is the corrosion rate in mils per year (mpy),
k is a unit adjusting constant ($3.45 \times 10^6$ for mpy),
$\Delta m$ is the mass loss in grams,
A is the surface area exposed in square centimeters
t is the time of exposure in hours, and
$\rho$ is the density in grams per cubic centimeter The corrosion rates for the two coupons calculated out to be:

| Coupon | 21 days | 67 days |
| --- | --- | --- |
| C-1018-1 | 0.27 mpy | 0.09 mpy |
| C-1018-2 | 1.01 mpy | 0.32 mpy |

No pitting was observed in either coupon. Since the only difference in the calculation of corrosion rate between the 21 day and 67 day exposures is the length of time, the 67 day data naturally shows a slower rate. The differences between the corrosion rate of coupon C-1018-2 and C-1018-1 might have resulted from erosional effects on C-1018-2, the coupon nearer the leading edge of the coupon holder. In any event, the difference is well within experimental error. As a means of comparison, a rod-type coupon inserted into a highly turbulent zone near the surface, experienced corrosion rates of 35.09 mpy and 11.0 mpy during the same 21 and 67 day periods. Such high rates (which are obviously predominantly erosion, rather than corrosion), if believed, would mislead the Corrosion Engineer regarding the effectiveness of his/her corrosion mitigation program and suggest a higher (more expensive) application rate.

By accurately duplicating flow conditions within the tubing string while minimizing the restriction to flow, the corrosion coupon anchoring system of the present invention enables a more accurate assessment of actual corrosion rate to be made. Accordingly, more accurate assessments of (1) the nature of the downhole corrosion problem, (2) the effectiveness of the corrosion mitigation program and (3) the life of the tubing, can be made.

Various changes, alternatives and modifications will be apparent following a reading of the foregoing application. For example, although the coupon holder of the present invention is depicted as housing two coupons, the length of the holder could be increased to accomodate anywhere from 3 to 6 coupons of various materials by simply adding additional center retainers. This would enable a variety of materials to be used in virtually identical environments to determine which material performed best in these downhole conditions for application to design considerations in associated wells. Accordingly, it is intended that all such changes, alternatives and modifications as come within the scope of the appended claims be considered part of the present invention.

I claim:

1. Apparatus for anchoring at least one tubular corrosion coupon at a preselected location downhole in a well that is producing a flow stream of well fluids in a section of cylindrical tubing string that is lacking a side pocket mandrel, said apparatus comprising:
    (a) a locking mandrel for positively locating said at least one tubular corrosion coupon directly in said flow stream at said preselected location by interlocking within a portion of said cylindrical tubing string section such that said flow stream passes through said corrosion coupon, said locking mandrel having a predetermined minimum inner diameter;
    (b) a cylindrical housing with a given inner dimension surrounding said tubular corrosion coupon, the inner dimension of the portion of said housing which is occupied by said coupon having a minimum dimension not less than said predetermined minimum inner diameter of said locking mandrel;
    (c) means connecting said cylindrical housing to said locking mandrel; and
    (d) means for securing said tubular corrosion coupon in said cylindrical housing.

2. The corrosion coupon anchoring apparatus of claim 1 wherein the means for connecting said cylindrical housing to said locking mandrel includes an adaptor which threadingly engages each of said housing and said mandrel.

3. The corrosion coupon anchoring apparatus of claim 1 wherein said means for securing said at least one tubular corrosion coupon in said cylindrical housing includes non-penetrating fastening means.

4. The corrosion coupon anchoring apparatus of claim 1 wherein said at least one tubular corrosion coupon comprises at least two tubular corrosion coupons.

5. The corrosion coupon anchoring apparatus of claim 4 wherein said two tubular corrosion coupons are each constructed of the same material.

6. The corrosion coupon anchoring apparatus of claim 4 wherein said two tubular corrosion coupons are each constructed of different material.

7. The corrosion coupon anchoring apparatus of claim 4 wherein said coupons are positioned axially one after the other in said flow stream, said means for securing said corrosion coupons in said cylindrical housing including a center retainer which telescopically receives one end of each of said tubular corrosion coupons.

8. The corrosion coupon anchoring apparatus of claim 7 wherein said means for securing said corrosion coupons in said cylindrical housing further comprises two end retainers, one each of which engage the distal ends of said two corrosion coupons.

9. The corrosion coupon anchoring apparatus of claim 8 wherein said center retainer and said two end retainers each have longitudinally extending grooves to permit flow of fluid on the exterior of said coupon.

10. The corrosion coupon anchoring apparatus of claim 2 wherein said means for securing said at least one corrosion coupon comprises two end retainers for compressively engaging the distal ends of said at least one corrosion coupon.

11. The corrosion coupon anchoring apparatus of claim 10 wherein one of said end retainers is engaged by an abutment formed within said cylindrical housing.

12. The corrosion coupon anchoring apparatus of claim 11 wherein the other of said end retainers is engaged by a beveled end of said adaptor.

13. The corrosion coupon anchoring apparatus of claim 12 wherein said abutment in the cylindrical housing and said beveled end on said adaptor firmly engage said end retainers with a limited compressive force which, in turn, firmly engage said at least one corrosion coupon without incurring or inflicting substantial deformation.

14. The corrosion coupon anchoring apparatus of claim 10 wherein said two end retainers each have longitudinally extending grooves to permit flow of fluid on the exterior of said coupon.

15. The corrosion coupon anchoring apparatus of claim 4 wherein said tubular member has an internal diameter that is not less than the minimum internal diameter of said locking mandrel.

16. A method of monitoring the downhole corrosive effects of well fluids on cylindrical production tubing of a well producing a flow stream of oil, and/or gas, comprising positioning at least one tubular coupon within a coupon holder, securing said at least one coupon in said holder using non-penetrating fastener means, anchoring said holder directly in the flow stream within said cylindrical production tubing at a predetermined location in said tubing such that the flow stream passes through said tubular coupon thereby exposing said at least one coupon to the same corrosive and flow conditions experienced by said cylindrical production tubing for a predetermined period of time, retrieving said at least one coupon in said coupon holder from said anchored position, determining the amount and nature of corrosion that has occurred in said predetermined period of time.

17. The method of claim 16 wherein said securing step is performed by telescoping a retainer over each end of said at least one coupon and applying a limited axially compressive force to and through the two retainers.

18. Apparatus for anchoring at least one corrosion coupon at a preselected location downhole in a tubing string of a producing well, said apparatus comprising:
(a) a locking mandrel for positively locating said at least one corrosion coupon at said preselected location by interlocking within a portion of said tubing string, said locking mandrel having a predetermined minimum inner diameter;
(b) a cylindrical housing with a given inner dimension surrounding said corrosion coupon, the inner dimension of the portion of said housing which is occupied by said coupon having a minimum dimension not less than said predetermined minimum inner diameter of said locking mandrel;
(c) means connecting said cylindrical housing to said locking mandrel; and
(d) two end retainers for compressively engaging the distal ends of said at least one corrosion coupon to secure said at least one coupon between them in said cylindrical housing.

19. The corrosion coupon anchoring apparatus of claim 18 wherein one end of each of said end retainers telescopically receives an end of said at least one coupon and the opposite ends of said end retainers are each beveled, the beveled end of one of said retainers being compressively engaged by a first inclined surface formed within said cylindrical housing and the beveled end of the other one of said retainers is compressively engaged by a second inclined surface.

* * * * *

UNITED STATES PATENT AND TRADEMARK OFFICE

CERTIFICATE

Patent No. 4,688,638                    Patented:   August 25, 1987

On petition requesting issuance of a certificate for correction
of inventorship pursuant to 35 USC 256, it has been found that
the above-identified patent, through error and without any
deceptive intent, improperly sets forth the inventorship.
Accordingly, it is hereby certified that the correct inventorship
of this patent is Mitchel E. Williams, Michael J. Bednarz, and Jon
R. Bryant.

Signed and Sealed this 14th Day of March 1989.

Abraham Hershkovitz
Petitions Examiner
Office of the Deputy Assistant
  Commissioner for Patents